United States Patent [19]

Descroix-Vagne et al.

[11] Patent Number: 5,668,109
[45] Date of Patent: Sep. 16, 1997

[54] PEPTIDES FOR INHIBITING PEPSIN RELEASE

[75] Inventors: Monique Descroix-Vagne, St-Cyr-Au-Mont-D'Or; Danielle Pansu, Lons-le Saunier; Thierry Tarrade, Gif sur Yvette, all of France

[73] Assignee: Societe de Conseils de Recherches et D'Applications Scientifiques (S.C.R.A.S.), France

[21] Appl. No.: 404,512

[22] Filed: Mar. 15, 1995

[30] Foreign Application Priority Data

Mar. 16, 1994 [GB] United Kingdom ............... 9405162

[51] Int. Cl.$^6$ ....................................... A61K 38/00
[52] U.S. Cl. ................... 514/13; 514/14; 514/15; 514/16; 514/17; 530/326; 530/327; 530/328; 530/329; 530/330
[58] Field of Search .................. 514/13, 14, 15, 514/16, 17; 530/326, 327, 328, 329, 330

[56] References Cited

FOREIGN PATENT DOCUMENTS

| 2298334 | 8/1976 | France . |
|---|---|---|
| 2601020 | 8/1988 | France . |
| 8906241 | 7/1989 | WIPO . |
| 93320 | 10/1991 | WIPO . |
| 9525123 | 9/1995 | WIPO . |

OTHER PUBLICATIONS

Gastroenterology (1992), 103(5), 1568–73 Charpin, Ghislaine et al. Effect of sorbin on duodenal absorpiton of water and electrolytes in the rat.

Nicol et al., "Pharmacokinetics and Organ Distribution of the Sorbin C–Terminal Peptides." *Peptides*, 15(6), 1994, 1013–1019.

*Primary Examiner*—Cecilia J. Tsang
*Assistant Examiner*—Cybille Delacroix-Muirheid
*Attorney, Agent, or Firm*—Bierman, Muserlain & Lucas

[57] ABSTRACT

Peptides derived from the C terminal sequence of sorbin, but containing at least one D-amino acid residue, inhibit pepsin release and are therefore likely to be useful in the treatment of ulcers or oesophagitis. Their salts and substitution derivatives are also claimed as a pharmaceutical compositions containing them. A method for the treatment of a patient suffering from gastric ulcers or oesophagitis comprising the administration of said peptides, is also claimed.

25 Claims, No Drawings

PEPTIDES FOR INHIBITING PEPSIN RELEASE

The invention relates to peptides able to inhibit the release of pepsin, to substitution derivatives and salts of such peptides and to pharmaceutical compositions containing these peptides. The peptides may be of use in the treatment of diseases related to the release of pepsin, and more particularly the treatment of ulcers or oesophagitis.

A new peptide has recently been isolated from pig intestines; this peptide, known as sorbin, has 153 natural amino acids (WO 89/06241). Sorbin and its C terminal peptide fragments (up to 40 amino acid residues) are able to provoke an increase in the process of absorption by the mucosa. We have unexpectedly found that the modification of these peptide fragments by the insertion of at least one D-amino acid residue confers another biological activity on these modified peptide analogues: they inhibit the release of pepsin, a biological activity which unmodified peptides do not have.

This activity is particularly interesting in certain circumstances. Gastric digestion is the result of the action of enzymes, hydrochloric acid and pepsin. Pepsin is a protein; with gastrin it is also one of the main constituents of the gastric juice. Its main physiological role is the initiation of protein digestion. However, many studies have shown the significant role of pepsin in the formation of ulcers. Consequently, in certain circumstances it may be desirable to inhibit the release of pepsin at least in part.

The invention provides a peptide of the general formula I

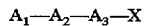  I in which:

$A_1$ represents the residue L-Thr or D-Thr; or one of the following sequences in which at least one amino acid residue may be of D configuration:

Val-Thr,
Pro-Val-Thr,
Arg-Pro-Val-Thr,
Glu-Arg-Pro-Val-Thr,
His-Glu-Arg-Pro-Val-Thr,
Gln-His-Glu-Arg-Pro-Val-Thr,
Leu-Gln-His-Glu-Arg-Pro-Val-Thr,
Ile-Leu-Gln-His-Glu-Arg-Pro-Val-Thr,
Ser-Ile-Leu-Gln-His-Glu-Arg-Pro-Val-Thr,
Ser-Ser-Ile-Leu-Gln-His-Glu-Arg-Pro-Val-Thr,
Lys-Ser-Ser-Ile-Leu-Gln-His-Glu-Arg-Pro-Val-Thr,
Gly-Lys-Ser-Ser-Ile-Leu-Gln-His-Glu-Arg-Pro-Val-Thr,
Pro-Gly-Lys-Ser-Ser-Ile-Leu-Gln-His-Glu-Arg-Pro-Val-Thr or
Glu-Pro-Gly-Lys-Ser-Ser-Ile-Leu-Gln-His-Glu-Arg-Pro-Val-Thr;

$A_2$ represents the sequence Lys-Pro-Gln-Ala in which at least one amino acid residue may be of D configuration;

$A_3$ represents a covalent bond or the sequence Gly-$A_4$-$A_5$ in which each of $A_4$ and $A_5$ independently represents a basic amino acid residue; and X represents a hydroxy, amino or alkylamino group; with the proviso that the peptide contains at least one D-amino acid residue.

The invention also provides substitution derivatives of the peptides of the general formula I in which one or more of the amino acid residues is substituted by a protecting group or protecting groups conventionally employed in peptides intended for biological use; when there are two or more protecting groups, they need not be the same. Preferably, the protecting groups are selected from lower alkyl, such as methyl or t-butyl; phenyl; benzyl or substituted benzyl such as trimethoxybenzyl; 2-chlorobenzyloxycarbonyl; 9-fluorenylmethyloxycarbonyl (Fmoc); t-butoxycarbonyl (Boc); acetyl; sulphonyl; and phosphoryl groups.

The invention further provides peptides containing the amino acid sequence $A_1$-$A_2$-$A_3$, in which $A_1$, $A_2$ and $A_3$ are as defined above.

The invention yet further provides pharmaceutically acceptable salts of peptides as defined above. These salts may be obtained with organic acids such as acetic, lactic, palmoic, maleic, citric, malic, ascorbic, benzoic, salicylic, succinic, methylsulphonic and toluenesulphonic acids; mineral acids such as hydrochloric, sulphuric or phosphoric acids; or polymeric acids such as tannic acid or carboxymethyl cellulose.

Each of $A_4$ and $A_5$, when present in peptides according to the invention, preferably independently represents a Lys, D-Lys, Arg or D-Arg residue.

As noted above, the peptides according to the invention contain one or more D-amino acid residues. When there is one, it is preferably the N terminal residue or the C terminal residue. When there are two, one is preferably the C terminal residue; the other may be located at any position, but is preferably the N-terminal residue. The preferred peptides are those in which $A_2$ represents Lys-Pro-Gln-D-Ala and $A_3$ represents a covalent bond. Preferred substitution derivatives of the peptides include those in which Lys residues bear acetyl protecting groups.

Examples of the preferred peptides according to the invention are the following:

Thr-Lys-Pro-Gln-D-Ala-NH$_2$,
Thr-Lys-Pro-Gln-D-Ala-Gly-Lys-Lys-NH$_2$,
Thr-(acetyl)Lys-Pro-Gln-D-Ala-NH$_2$,
Pro-Val-Thr-Lys-Pro-Gln-D-Ala-NH$_2$,
Pro-D-Val-Thr-Lys-Pro-Gln-Ala-NH$_2$,
Pro-Val-Thr-Lys-Pro-Gln-Ala-Gly-Arg-D-Arg,
Pro-Val-Thr-(acetyl)Lys-Pro-Gln-D-Ala-NH$_2$,
D-Pro-Val-Thr-Lys-Pro-Gln-Ala-NH$_2$,
His-Glu-Arg-Pro-Val-Thr-Lys-Pro-Gln-D-Ala-NH$_2$,
Ile-Leu-Gln-His-Glu-Arg-Pro-Val-Thr-Lys-Pro-Gln-D-Ala-NH$_2$,
Glu-Pro-Gly-Lys-Ser-Ser-Ile-Leu-Gln-His-Glu-Arg-Pro-Val-Thr-Lys-Pro-Gln-D-Ala-NH$_2$,
D-Pro-Val-Thr-Lys-Pro-Gln-D-Ala-NH$_2$,
D-Pro-Val-Thr-Lys-Pro-Gln-Ala-Gly-D-Lys-Lys-NH$_2$,
Pro-D-Val-Thr-Lys-Pro-Gln-D-Ala-NH$_2$ and
D-Pro-Val-Thr-(acetyl)Lys-Pro-Gln-D-Ala-NH$_2$.

The peptides according to the invention may be prepared by any of the conventional peptide synthesis methods. For example, they may advantageously be prepared by solid phase synthesis carded out as follows: the formation of the peptide chain begins with the fixing of the C terminal amino acid of the chain via its carboxy group to a resin; the amino function is protected with a protecting group such as Boc. After fixing the C terminal amino acid to the resin, its amine function is deprotected by washing the resin with an acid. In the case of protection with Boc, deprotection can take place by washing with trifluoroacetic acid. The second amino acid, the amine function of which is protected, is then coupled via its carboxy group to the deprotected amino function of the C terminal amino acid of the chain. This coupling preferably takes place in the presence of a coupling agent such as dicyclohexylcarbodiimide or diisopropylcarbodiimide. The peptide chain thus formed comprises two amino acids, the end amine function of which is protected. As before, this end amine function is deprotected and the fixing of the third amino acid can take place. The desired peptide chain is thus obtained by fixing the amino acids one after the other. After elimination of all the protecting groups, the peptide is detached from the resin.

The synthesis of a peptide of the invention, Pro-Val-Thr-Lys-Pro-Gln-D-Ala-NH$_2$, is described briefly below. Other peptides of the invention can be prepared by suitable modifications of this peptide synthesis.

The synthesis is carried out in the solid phase at ambient temperature. The method used comprises the following stages: deprotection, neutralisation and coupling. The resin used is of the cross-linked polystyrene type with 1% divinyl benzene (Merrified resin). Boc-D-Ala is fixed to the Merrifield resin in the presence of caesium carbonate in toluene and dimethylformamide (DMF). The terminal amine function of the amino acids used is protected by the Boc group. These Boc groups are displaced by trifluoroacetic acid followed by several washings with dichloromethane and isopropanol. The amino groups are neutralised with triethylamine followed by several washings. The threonine and valine are transformed before coupling into an ester of hydroxybenzotriazole in the presence of diisopropylcarbodiimide (DIPCDI); for glutamine, the ester of hydroxybenzotriazole is formed directly in the reactor. The lysine and the two prolines are transformed into symmetrical anhydride before coupling. In all cases, coupling takes place in the presence of diisopropylethylamine. The side chain of the lysine is protected by an Fmoc grouping, whereas that of the threonine is not protected. On completion of the last coupling, the Fmoc grouping is displaced by piperidine in DMF before displacement of the Boc protecting group from the N terminal amine function of the proline. The peptide is obtained by cleavage of the resin after treatment in ammonia in a methanol/DMF mixture. The crude product thus obtained is then purified.

The invention additionally provides a pharmaceutical composition comprising a peptide of the general formula I as defined above, a substitution derivative of such a peptide as defined above or a peptide including the amino acid sequence $A_1$-$A_2$-$A_3$ as defined above, in admixture with a phamaceutically acceptable diluent or carrier.

Finally, the invention provides a method for the treatment of a patient suffering from gastric ulcers or oesophagitis, the method comprising administering to the patient an effective amount of a peptide of the general formula I as defined above, a substitution derivative of such a peptide as defined above or a peptide including the amino acid sequence $A_1$-$A_2$-$A_3$ as defined above, alone or in admixture with a pharmaceutically acceptable diluent or carrier.

The peptides of the invention can be administered by the oral, intravenous, parenteral, subcutaneous, intraperitoneal or intramuscular routes.

The pharmaceutical composition may take the form of a capsule, a tablet, a lyophilate or a liquid depending on the method of administration selected. The pharmaceutical composition may also take the form of a prolonged release formulation.

By the oral route, peptides according to the invention may be administered in man at a dose of 5 to 100 µg/kg per day. By the intravenous or subcutaneous route, peptides according to the invention may be administered in man at a dose of 1 to 12 µg/kg one to three times per day. In the animal, the preparations according to the invention are found in large quantities in the organism several days after one acute administration, and more particularly the peptide Pro-Val-Thr-Lys-Pro-Gln-D-Ala-NH$_2$ which is found in quantities greater than 10%.

Toxicity.

The subacute toxicity was studied in the rat and the dog. Following administrations of doses up to 4000 µg/kg/d, no sign of toxicity and no signs suggesting a mutagenic power were observed four weeks after administration. In man, a subcutaneous or intravenous injection at the dose of 200 µg/kg causes no biological, clinical or pathological anomaly.

Pharmacology

The therapeutical interest of the peptides of the invention has been established by the following experiment.

The intensity of the gastric response is measured by determining the volume of gastric secretion induced.

Cats were operated on under general anaesthetic; the operation allowed the stomach to be divided into two parts: Heidenheim's pouch and the gastric fistula. These two pouches are diverted to the outside in order to recover the secretions of hydrochloric acid, pepsin and gastric juices, once during the basal phase and then after stimulation. These cats have chronic fistulas: they can therefore undergo a number of tests each week and be their own controls. The secretion of pepsin is stimulated by administration to the living animals of pentagastrin (PG) and VIP (Vasoactive Intestinal Peptide) by perfusion for 2 hours at the rate of 2 and 4 µg/kg/h.

One hour after stimulation by pentagastrin and VIP, these peptides were added in perfusion at the dose of 100 pmol/kg/h. The volume of gastric juices was collected over the 30 minutes preceding perfusion until the end of perfusion. The quantity of pepsin in the gastric juice (as homogeneous as possible) was evaluated by a proteolytic spectrophotometric method.

The results obtained in 9 to 12 experiments are reported in the Tables below: the secretion of pepsin is expressed in mg/15 minutes, mean of 2 periods of 15 minutes per test during the basal secretion and mean of 6 periods of 15 minutes during the stimulated secretion.

Certain peptides of the invention with at least one D-amino acid residue are compared with their analogues in which all the amino acid residues are of L configuration.

TABLE 1

Comparison of the activity of a peptide of the invention
$P^D_1$: Pro—Val—Thr—Lys—Pro—Gln-D-Ala—NH$_2$.
with that of its analogue
$P_1$: Pro—Val—Thr—Lys—Pro—Gln—Ala—NH$_2$

|  | VIP + PG | VIP + PG + $P_1$ | VIP + PG + $P^D_1$ |
|---|---|---|---|
| Cat No 1 | 1.775 | 0.952 | 0.926 |
| Cat No 2 | 1.316 | 1.367 | 1.711 |
| Cat No 3 | 2.049 | 1.680 | 1.846 |
| Cat No 1 | 1.852 | 2.993 | 2.082 |
| Cat No 2 | 3.334 | 2.418 | 2.157 |
| Cat No 3 | 4.010 | 5.392 | 3.932 |
| Cat No 1 | 2.520 | 1.729 | 1.456 |
| Cat No 2 | 2.409 | 2.403 | 1.516 |
| Cat No 3 | 4.277 | 3.989 | 3.891 |
| Cat No 1 | 1.750 | — | — |
| Cat No 2 | 1.556 | — | — |
| Cat No 3 | 4.442 | — | — |
| Mean | 2.607 | 2.547 | 2.169 |
| Std Dev | 0.323 | 0.468 | 0.351 |

The numbers in the Table refer to the amount of pepsin secreted in mg/15 min.

TABLE 2

Activity of the peptides of the invention
$P^D_2$: D-Pro—Val—Thr—Lys—Pro—Gln—Ala—$NH_2$,
$P^D_3$: Pro—Val—Thr—(acetyl)Lys—Pro—Gln-D-Ala—$NH_2$
$P^D_4$: D-Pro—Val—Thr—Lys—Pro—Gln-D-Ala—$NH_2$

|  | VIP + PG | VIP + PG + $P^D_2$ | VIP + PG + $P^D_3$ | VIP + PG + $P^D_4$ |
|---|---|---|---|---|
| Cat no 1 | 6.727 | 2.689 | 2,317 | 4,427 |
| Cat no 2 | 4.773 | 2.007 | 1,860 | 2,999 |
| Cat no 3 | 4.324 | 2.576 | 0,891 | 2,898 |
| Cat no 4 | 2.458 | 2.076 | 1,725 | 3,780 |
| Cat no 5 | 3.744 | 2.689 | 2,630 | 3,740 |
| Cat no 6 | 3.276 | 1.143 | 2,217 | 3,147 |
| Cat no 7 | 2.708 | 2.409 | 1,899 | 2,452 |
| Cat no 8 | 3.991 | 3.172 | 4,321 | 3,996 |
| Cat no 9 | 0.384 | 1.036 | 0,738 | 0,236 |
| Cat no 10 | 5.184 | 3.164 | 3,811 | 3,362 |
| Mean | 3.757 | 2.296** | 2.241** | 3,104** |
| Std Dev | 0.544 | 0.235 | 0,358 | 0,368 |

The numbers in the Table refer to the amount of pepsin secreted in mg/15 min.

TABLE 3

Activity of the peptides of the invention
$P^D_5$: Pro-D-Val—Thr—Lys—Pro—Gln—Ala—$NH_2$,
$P^D_6$: Pro-D-Val—Thr—Lys—Pro—Gln-D-Ala—$NH_2$
$P^D_7$: D-Pro—Val—Thr—(acetyl)Lys—Pro—Gln-D-Ala—$NH_2$

|  | VIP + PG | VIP + PG + $P^D_5$ | VIP + PG + $P^D_6$ | VIP + PG + $P^D_7$ |
|---|---|---|---|---|
| Cat No 1 | 6.727 | 4.263 | 2.480 | 2.163 |
| Cat No 2 | 4.773 | 2.435 | 2.544 | 2.995 |
| Cat No 3 | 4.324 | 1.317 | 2.589 | 1.441 |
| Cat No 4 | 2.458 | 3.191 | 3.110 | 2.834 |
| Cat No 5 | 3.744 | 2.727 | 4.142 | 1.236 |
| Cat No 6 | 3.276 | 3.486 | 1.710 | 2.047 |
| Cat No 7 | 2.708 | 2.634 | 2.370 | 2.544 |
| Cat No 8 | 3.991 | 2.852 | 4.165 | 3.971 |
| Cat No 9 | 0.384 | 1.132 | 1.693 | 1.520 |
| Cat No 10 | 5.184 | 3.804 | 2.931 | 3.402 |
| Mean | 3.757 | 2.784 | 2.773 | 2.415 |
| Std Dev | 0.544 | 0.315 | 0.270 | 0.284 |

The numbers in the Table refer to the amount of pepsin secreted in mg/15 min.

TABLE 4

Activity of the peptides of the invention
$P^D_8$: His—Glu—Arg—Pro—Val—Thr—Lys—Pro—Gln-D-Ala—$NH_2$
$P^D_9$: Ile—Leu—Gln—His—Glu—Arg—Pro—Val—Thr—Lys—Pro—Gln-D-Ala—$NH_2$
$P^D_{10}$: Glu—Pro—Gly—Lys—Ser—Ser—Ile—Leu—Gln—His—Glu—Arg—Pro—Val—Thr—Lys—Pro—Gln-D-Ala—$NH_2$.

|  | VIP + PG | VIP + PG + $P^D_8$ | VIP + PG + $P^D_9$ | VIP + PG + $P^D_{10}$ |
|---|---|---|---|---|
| Cat no 1 | 3.832 | 3.117 | 2.409 | 2.691 |
| Cat no 2 | 1.826 | 2.730 | 1.440 | 1.764 |
| Cat no 3 | 2.132 | 1.690 | 1.964 | 2.520 |
| Cat no 4 | 3.891 | 1.725 | 2.259 | 2.410 |
| Cat no 5 | 2.042 | 2.076 | 1.230 | 2.833 |
| Cat no 6 | 3.250 | 1.358 | 1.580 | 2.877 |
| Cat no 7 | 4.014 | 2.452 | 2.488 | 1.726 |
| Cat no 8 | 4.280 | 2.689 | 2.426 | 2.015 |
| Cat no 9 | 3.273 | 2.920 | 3.790 | 1.953 |
| Mean | 3.171 | 2.306* | 2.176* | 2.310* |
| Std Dev | 0.313 | 0.206 | 0.254 | 0.151 |

The numbers in the Table refer to the amount of pepsin secreted in mg/15 min.

TABLE 5

Comparison of the activity of a peptide of the invention
$P^D_8$: His—Glu—Arg—Pro—Val—Thr—Lys—Pro—Gln-D-Ala—$NH_2$
with that of its analogue
$P_8$ His—Glu—Arg—Pro—Val—Thr—Lys—Pro—Gln—Ala—$NH_2$

|  | VIP + PG | VIP + PG + $P_8$ | VIP + PG + $P^D_8$ |
|---|---|---|---|
| Cat no 1 | 4.385 | 3.693 | 2.717 |
| Cat no 2 | 4.460 | 4.915 | 4.630 |
| Cat no 3 | 3.079 | 3.350 | 2.198 |
| Cat no 4 | 3.333 | 2.442 | 1.746 |
| Cat no 1 | 3.410 | 3.896 | 2.270 |
| Cat no 2 | 2.510 | 2.432 | 2.245 |
| Cat no 3 | 2.764 | 1.626 | 2.452 |
| Cat no 4 | 2.191 | 1.925 | 2.247 |
| Cat no 5 | 4.908 | 5.012 | 2.739 |
| Mean | 3.449 | 3.255 | 2.583* |
| Std Dev | 0.314 | 0.412 | 0.274 |

The numbers in the Table refer to the amount of pepsin secreted in mg/15 min.

TABLE 6

Activity of the peptides of the invention
$P^D_{11}$: Thr—Lys—Pro—Gln-D-Ala—$NH_2$
$P^D_{12}$: Thr-(acetyl)Lys—Pro—Gln-D-Ala—$NH_2$

|  | VIP + PG | VIP + PG + $P^D_{11}$ | VIP + PG + $P^D_{12}$ |
|---|---|---|---|
| Cat no 1 | 3.217 | 3.452 | 2.620 |
| Cat no 2 | 3.772 | 3.114 | 1.925 |
| Cat no 3 | 3.580 | 3.348 | 4.037 |
| Cat no 4 | 2.166 | 2.181 | 1.896 |
| Cat no 5 | 6.562 | 2.219 | 3.585 |
| Cat no 6 | 2.290 | 1.638 | 2.192 |
| Cat no 7 | 2.008 | 3.291 | 0.625 |
| Cat no 8 | 2.034 | 2.076 | 1.339 |
| Cat no 9 | 2.548 | 0.850 | 1.385 |
| Mean | 3.131 | 2.463 | 2.178* |
| Std Dev | 0.484 | 0.299 | 0.364 |

The numbers in the Table refer to the amount of pepsin secreted in mg/15 min.

We claim:

1. A peptide of the general formula I $$A_1-A_2-A_3-X \qquad I$$

in which:

$A_1$ represents the residue L-Thr or D-Thr; or one of the following sequences in which at least one amino acid residue may be of D configuration:

Val-Thr,

Pro-Val-Thr,

Arg-Pro-Val-Thr,

Glu-Arg-Pro-Val-Thr,

His-Glu-Arg-Pro-Val-Thr,

Gln-His-Glu-Arg-Pro-Val-Thr,

Leu-Gln-His-Glu-Arg-Pro-Val-Thr,

Ile-Leu-Gln-His-Glu-Arg-Pro-Val-Thr,

Ser-Ile-Leu-Gln-His-Glu-Arg-Pro-Val-Thr,

Ser-Ser-Ile-Leu-Gln-His-Glu-Arg-Pro-Val-Thr,

Lys-Ser-Ser-Ile-Leu-Gln-His-Glu-Arg-Pro-Val-Thr,

Gly-Lys-Ser-Ser-Ile-Leu-Gln-His-Glu-Arg-Pro-Val-Thr,

Pro-Gly-Lys-Ser-Ser-Ile-Leu-Gln-His-Glu-Arg-Pro-Val-Thr or

Glu-Pro-Gly-Lys-Ser-Ser-Ile-Leu-Gln-His-Glu-Arg-Pro-Val-Thr;

$A_2$ represents the sequence Lys-Pro-Gln-Ala in which at least one amino acid residue may be of D configuration;

$A_3$ represents a covalent bond or the sequence Gly-$A_4$-$A_5$ in which each of $A_4$ and $A_5$ independently represents a basic amino acid residue; and X represents a hydroxy, amino or alkylamino group; with the proviso that the peptide contains at least one D-amino acid residue.

2. A peptide containing the amino acid sequence $A_1$-$A_2$-$A_3$, in which $A_1$, $A_2$ and $A_3$ are as defined in claim 1, the peptide containing at least one D-amino acid residue.

3. A peptide according to claim 1 or 2 in which one or more of the amino acid residues is substituted by a protecting group or protecting groups, when there are two or more protecting groups, they need not be the same.

4. A peptide according to claim 3 containing at least one acetyl protected lysin residue.

5. A peptide according to claim 1 in the form of its pharmaceutically acceptable salt.

6. A peptide according to claim 1 in which the C-terminal amino acid residue is of D-configuration.

7. A peptide according to claim 1 in which the N-terminal amino acid residue is of D-configuration.

8. A peptide according to claim 1 in which $A_2$ represents Lys-Pro-Gln-D-Ala and $A_3$ represents a covalent bond.

9. A peptide of the formula Thr-Lys-Pro-Gln-D-Ala-$NH_2$.

10. A peptide of the formula Thr-Lys-Pro-Gln-D-Ala-Gly-Lys-Lys-$NH_2$.

11. A peptide of the formula Thr-(acetyl)Lys-Pro-Gln-D-Ala-$NH_2$.

12. A peptide of the formula Pro-Val-Thr-Lys-Pro-Gln-D-Ala-$NH_2$.

13. A peptide of the formula Pro-D-Val-Thr-Lys-Pro-Gln-Ala-NH2.

14. A peptide of the formula Pro-Val-Thr-Lys-Pro-Gln-Ala-Gly-Arg-D-Arg.

15. A peptide of the formula Pro-Val-Thr-(acetyl)Lys-Pro-Gln-D-Ala-$NH_2$.

16. A peptide of the formula D-Pro-Val-Thr-Lys-Pro-Gln-Ala-$NH_2$.

17. A peptide of the formula His-Glu-Arg-Pro-Val-Thr-Lys-Pro-Gln-D-Ala-$NH_2$.

18. A peptide of the formula Ile-Leu-Gln-His-Glu-Arg-Pro-Val-Thr-Lys-Pro-Gln-D-Ala-$NH_2$.

19. A peptide of the formula Glu-Pro-Gly-Lys-Ser-Ser-Ile-Leu-Gln-His-Glu-Arg-Pro-Val-Thr-Lys-Pro-Gln-D-Ala-$NH_2$.

20. A peptide of the formula D-Pro-Val-Thr-Lys-Pro-Gln-D-Ala-$NH_2$.

21. A peptide of the formula D-Pro-Val-Thr-Lys-Pro-Gln-Ala-Gly-D-Lys-Lys-$NH_2$.

22. A peptide of the formula Pro-D-Val-Thr-Lys-Pro-Gln-D-Ala-$NH_2$.

23. A peptide of the formula D-Pro-Val-Thr-(acetyl)Lys-Pro-Gln-D-Ala-$NH_2$.

24. A pharmaceutical composition comprising a peptide according to claim 1 in admixture with a pharmaceutically acceptable diluent or carrier.

25. Method for the treatment of a patient suffering from gastric ulcers or oesophagitis, the method comprising administering to the patient an effective amount of a peptide according to claim 1, alone or in admixture with a pharmaceutically acceptable diluent or carrier.

* * * * *